United States Patent
Park et al.

(10) Patent No.: US 9,629,950 B2
(45) Date of Patent: Apr. 25, 2017

(54) EXTERIOR CAP OF TRANSFER SET FOR PERITONEAL DIALYSIS

(71) Applicant: Research Cooperation Foundation of Yeungnam University, Gyeongsan-si, Gyeongsangbuk-do (KR)

(72) Inventors: Jong Won Park, Seoul (KR); Sang Ho Ahn, Daegu (KR); Joon Ha Lee, Daegu (KR); Il Gwon Jung, Daegu (KR)

(73) Assignee: RESEARCH COOPERATION FOUNDATION OF YEUNGNAM UNIVERSITY, Gyeongsangbuk-Do (KR)

( * ) Notice: Subject to any disclaimer, the term of this patent is extended or adjusted under 35 U.S.C. 154(b) by 269 days.

(21) Appl. No.: 14/578,499

(22) Filed: Dec. 22, 2014

(65) Prior Publication Data
US 2015/0112249 A1 Apr. 23, 2015

Related U.S. Application Data

(63) Continuation of application No. PCT/KR2012/011306, filed on Dec. 21, 2012.

(30) Foreign Application Priority Data

Jun. 22, 2012 (KR) .......... 10-2012-0067532

(51) Int. Cl.
| | |
|---|---|
| A61M 1/00 | (2006.01) |
| A61M 1/28 | (2006.01) |
| A61M 39/20 | (2006.01) |
| A61M 39/10 | (2006.01) |

(52) U.S. Cl.
CPC .............. *A61M 1/28* (2013.01); *A61M 1/285* (2013.01); *A61M 39/10* (2013.01); *A61M 39/20* (2013.01); *A61M 2039/1066* (2013.01)

(58) Field of Classification Search
CPC .................... A61M 1/28; A61M 1/285; A61M 2039/1066; A61M 39/10; A61M 39/20
See application file for complete search history.

(56) References Cited

U.S. PATENT DOCUMENTS

| | | |
|---|---|---|
| 4,642,091 A | 2/1987 | Richmond |
| 4,655,762 A | 4/1987 | Rogers |
| 6,152,913 A | 11/2000 | Feith et al. |

(Continued)

FOREIGN PATENT DOCUMENTS

WO 03-068293 A2 8/2003

OTHER PUBLICATIONS

International Search Report for PCT/KR2012/011306 mailed Apr. 1, 2013 from Korean Intellectual Property Office.

*Primary Examiner* — Rebecca E Eisenberg
(74) *Attorney, Agent, or Firm* — Revolution IP, PLLC (57) ABSTRACT

An exterior cap of transfer set for peritoneal dialysis, including: a cylindrical cap unit to which the end connector of the peritoneal transfer set is coupled; a guide unit that is coupled to the cap unit, extends to the peritoneal transfer set to provide an expanding internal space, and guides the end connector of the peritoneal transfer set into the cap unit; and a coupling-separating unit that combines the cap unit and the guide unit with each other and separates the cap unit and the guide unit in accordance with selection of a user.

18 Claims, 5 Drawing Sheets

(56) References Cited

U.S. PATENT DOCUMENTS

7,374,555 B2 * 5/2008 Heinz ................ A61M 5/5086
            604/111
8,177,760 B2   5/2012 Rome et al.

* cited by examiner

EXTERIOR CAP OF TRANSFER SET FOR PERITONEAL DIALYSIS

CROSS REFERENCE TO PRIOR APPLICATIONS

This application is a Continuation of PCT International Patent Application No. PCT/KR2012/011306 filed on Dec. 21, 2012, which claims priority to Korean Patent Application No. 10-2012-0067532 filed on Jun. 22, 2012, which are all hereby incorporated by reference in their entirety.

BACKGROUND

The present invention relates to a exterior cap of transfer set for peritoneal dialysis, and more particularly, to a exterior cap of transfer set for peritoneal dialysis which prevents exogenous infection of a peritoneal dialysis patient through a peritoneal transfer set by being hermetically coupled to an end connector of a peritoneal transfer set connected with an interperitonal catheter of the patient.

Referring to the background of Korean Patent No. 0539411, patients with acute and chronic renal failure generally need to receive one of three types of treatments, that is, peritoneal dialysis, hemodialysis, and kidney transplant. Although kidney transplant of those treatments is the most effective and sure treatment, there is a need for a donor of a kidney first and the operation is complicated, so a small number of patient can receive the benefits of kidney transplant and most patients with renal failure receive peritoneal dialysis or hemodialysis. Peritoneal dialysis, which has been developed at the end of 1970s has the advantage that the fee is lower than that of hemodialysis and patient can perform peritoneal dialysis by themselves even at home and office or during journey, such that patients are increasingly taking peritoneal dialysis.

Peritoneal dialysis (CAPD) is a treatment of putting a catheter in the peritoneal cavity of a patient and injecting a dialysate mainly composed of glucose and electrolyte into the peritoneal cavity through the catheter so that waste products or water in the blood is discharged outside through the peritoneum of the patient by an osmotic action.

In general, for patients who undergo peritoneal dialysis, a dialysate of about 2 liters is injected at a time, left in a peritoneal cavity for about 6 to 8 hours, and then replaced with a new dialysate. The catheter in the peritoneal cavity of a patient is connected with a dialysis kit with a dialysate therein through an end connector of a peritoneal transfer set and the patient has to repeat the process of connecting and disconnecting the peritoneal transfer set and the dialysis kit with a dialysate therein at least four times or more a day.

Accordingly, the end connector of the peritoneal transfer set may be infected by microorganisms in the air or the patient's hands. Such infection may cause fatal peritonitis to patients, so a disposable exterior cap with a disinfectant therein is hermetically connected to the end connector of the peritoneal transfer set while the end connector is not connected with a dialysis kit in order to prevent exogenous infection of patients. Accordingly, safety for patient against exogenous infection is ensured.

However, recently, peritoneal dialysis patients due to a chronic disease in peritoneal dialysis patients have been rapidly increasing and the case due to diabetic nephropathy of the patients is over 50% and diabetic retinopathy accompanies in most cases. Peritoneal dialysis patients accompanied by diabetic retinopathy are accompanied by altered vision, such that they have difficulty in connecting the exterior cap to the end connector of a peritoneal transfer set connected to a peritoneal cavity by themselves.

SUMMARY OF THE INVENTION

An object of the present invention is to provide a exterior cap for a peritoneal dialysis having a structure improved to be easily hermetically coupled to the end connector of a peritoneal transfer set even by a patient with altered vision.

The present invention provides a exterior cap of transfer set for peritoneal dialysis which prevents exogenous infection of a peritoneal dialysis patient through a peritoneal transfer set by being hermetically coupled to an end connector of a peritoneal transfer set connected with an interperitonal catheter of the patient. The exterior cap includes: a cylindrical cap unit to which the end connector of the peritoneal transfer set is coupled; a guide unit that is coupled to the cap unit, extends to the peritoneal transfer set to provide an expanding internal space, and guides the end connector of the peritoneal transfer set into the cap unit; and a coupling-separating unit that combines the cap unit and the guide unit with each other and separates the cap unit and the guide unit in accordance with selection of a user.

The guide unit may have a conical shape. The guide unit may be made of any one selected from a group of paper, PVC, and fiber.

According to an aspect of the present invention, the coupling-separating unit may couple the cap unit and the guide unit that are separated. To this end, the coupling-separating unit may have a bonding band that fixes the cap unit and the guide unit by bonding coupling ends of the cap unit and the guide unit. Further, the coupling-separating unit may further have first separation member that extends outward from an end of the bonding band so that a user easily holds the bonding band. The guide unit may further have a first cut-off portion defined by a pair of creases spaced from each other so that at least a side of the guide unit is partially cut. Further, the guide unit may further have a first cut-off member protruding outward at a side of the first cut-off portion so that a user holds the first cut-off member with fingers. Furthermore, the first cut-off portion and the bonding band may be connected to each other. The first cut-off portion may be formed longitudinally at a side of the guide unit, or the first cut-off portion may be formed circumferentially at a side of the guide unit, that is, spirally circumferentially formed to grow longitudinally.

According to another aspect of the present invention, the cap unit, the guide unit, and the coupling-separating unit may be integrally formed. The coupling-separating unit may have: a separating portion that is defined by a pair of creases spaced from each other at the joint of a cap unit and a guide unit; and a second separation member that protrudes outward at a side of the separating portion so that a user holds the second separation member with fingers. Further, the guide unit may further have a second cut-off portion defined by a pair of creases spaced from each other so that at least a side of the guide unit is partially cut. Furthermore, the guide unit may further have a second cut-off member protruding outward at a side of the second cut-off portion so that a user holds the second cut-off member with fingers. The second cut-off portion and the separating portion may be connected to each other. The second cut-off portion may be formed longitudinally at a side of the guide unit. Alternatively, the second cut-off portion may be formed circumferentially at a side of the guide unit. Alternatively, the second cut-off portion may be formed spirally circumferentially at a side of the guide unit to grow longitudinally.

According to the exterior cap of transfer set for peritoneal dialysis of the present invention, a peritoneal dialysis patient can easily couple the exterior cap to the end connector of the peritoneal transfer set, using the guide unit providing an internal space expanding to the end connector of the peritoneal transfer set and can separate the guide unit, which is unnecessary after the exterior cap is coupled, using the coupling-separating unit. Therefore, convenience for a user can be increased.

In particular, even a peritoneal dialysis patient accompanied by altered vision due to diabetic retinopathy can easily couple the exterior cap of the present invention by means of the guide unit providing an expanding internal space.

DETAILED DESCRIPTION

Hereinafter, exemplary embodiments of the present invention will be described with reference to accompanying drawings. The terms and words used in the present specification and claims should not be interpreted as being limited to typical meanings or dictionary definitions, but should be interpreted as having meanings and concepts relevant to the technical scope of the present invention based on the rule according to which an inventor can appropriately define the concept of the term to describe most appropriately the best method he or she knows for carrying out the invention.

Figure 1:
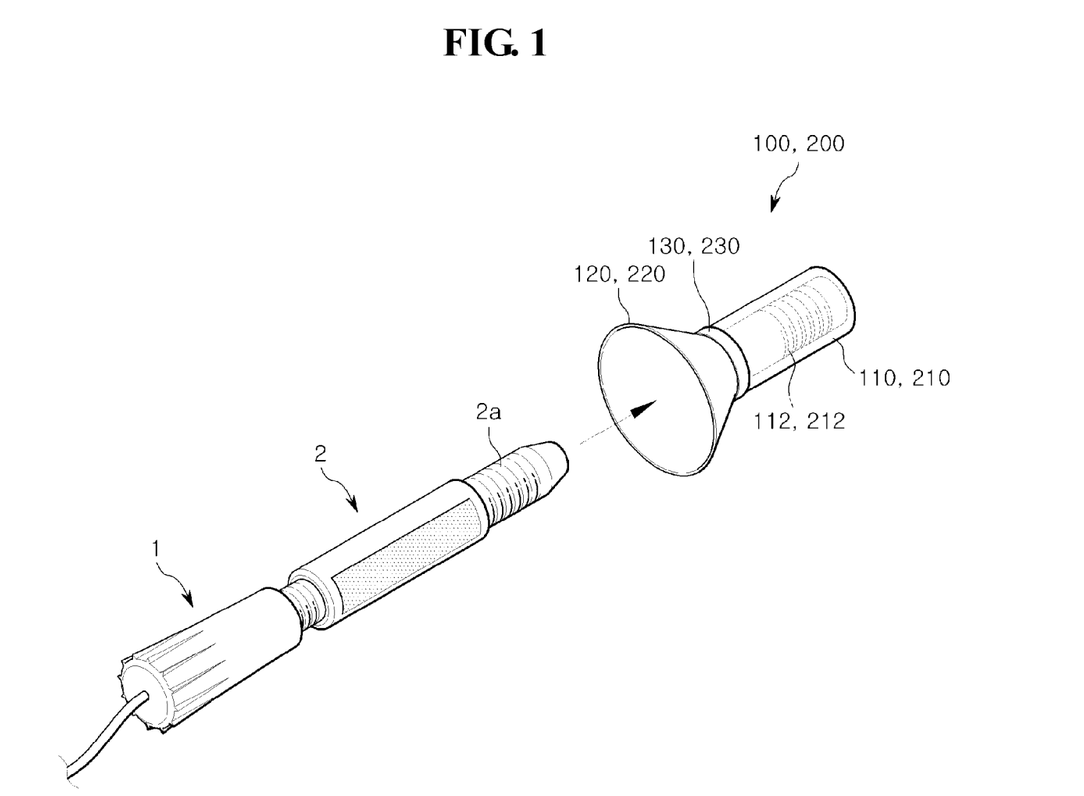
FIG. 1 is a perspective view illustrating a exterior cap of transfer set for peritoneal dialysis according to the present invention.

FIG. 1 is a perspective view illustrating a exterior cap of transfer set for peritoneal dialysis according to the present invention.

Referring to the figure, exterior caps 100 and 200 for a peritoneal dialysis transfer set (hereafter, referred to as a 'exterior cap') according to the present invention is provided to prevent exogenous infection of a patient through a peritoneal transfer set 1 connected with a catheter (not illustrated) in the peritoneal cavity of a peritoneal dialysis patient by being hermetically coupled to an end connector 2 of the peritoneal transfer set 1. To this end, the exterior caps 100 and 200 include cap units 110 and 210, guide units 120 and 220, and coupling-separating units 130 and 230, respectively.

The cap units 110 and 210 have a cylindrical shape and have an open end and a closed end. An end connector 2 of the peritoneal transfer set 1 is coupled to the open end of the cap units 110 and 210. To this end, female threads 112 and 212 are formed on the inner sides of the cap unit 110 and 210 and a male thread 2a formed on the outer side of the end connector 2 is inserted in the female threads 112 and 212, thereby combining the cap units 110 and 210 and the end connector 2 of the peritoneal transfer set 1.

The guide units 120 and 220 are coupled to the cap units 110 and 210 and extend to the peritoneal transfer set 1 to provide an expanding internal space, so they can guide the end connector 2 of the peritoneal transfer set 1 into the cap units 110 and 120. The guide units 120 and 220 may have, for example, a conical shape, as illustrated in the figures. The guide units 120 and 220 may be separated, after the end connector 2 of the peritoneal transfer set 1 is coupled to the cap unit 110. This is because the guide units 120 and 220 protrude from the abdominal region of a user (patient), so they may interfere with the user in everyday life.

The coupling-separating units 130 and 230 combine the cap units 110 and 210 and the guide units 120 and 220 with each other. However, a user (patient) may selectively separate the cap units 110 and 210 from the guide units 120 and 220, using the coupling-separating units 130 and 230.

The exterior caps 100 and 200 according to the present invention may be divided into a separable type and an integral type in accordance with whether the cap units 110 and 210 and the guide units 120 and 220 can be separated or not.

The exterior cap 100 (100a, 100b, 100c) according to an embodiment of the present invention in which the cap unit 110 and the guide unit 120 (120a, 120b, 120c) are implemented in a separable type.

Figure 2:
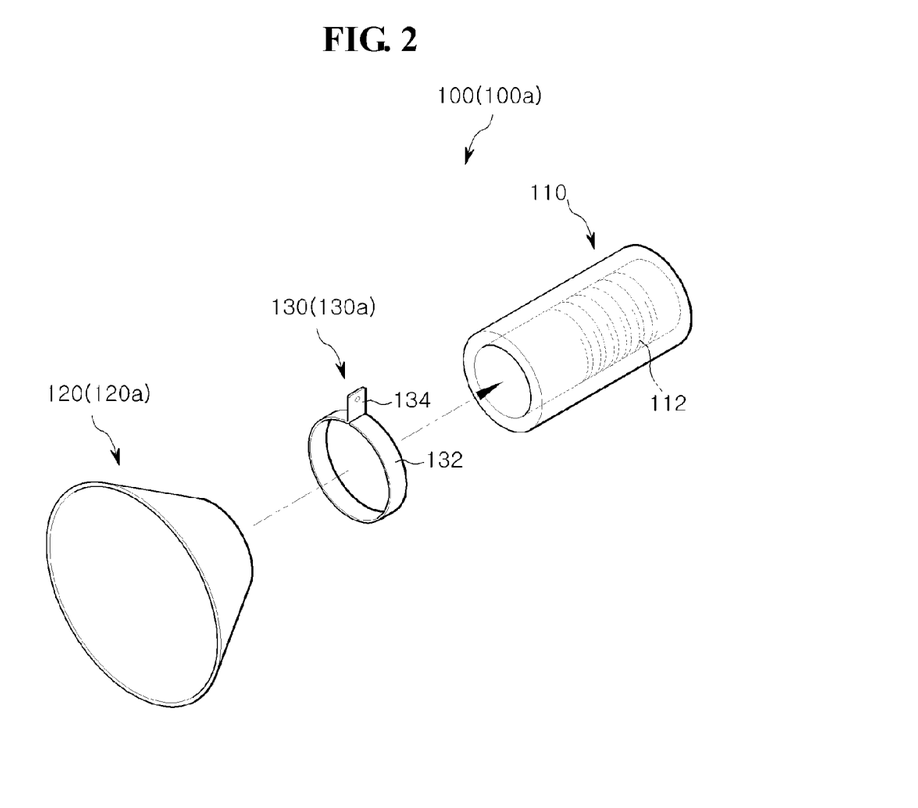
FIG. 2 is an exploded perspective view illustrating an embodiment of the present invention in which the cap unit and the guide unit of the exterior cap illustrated in FIG. 1 are implemented in a separable type.
Figure 3:
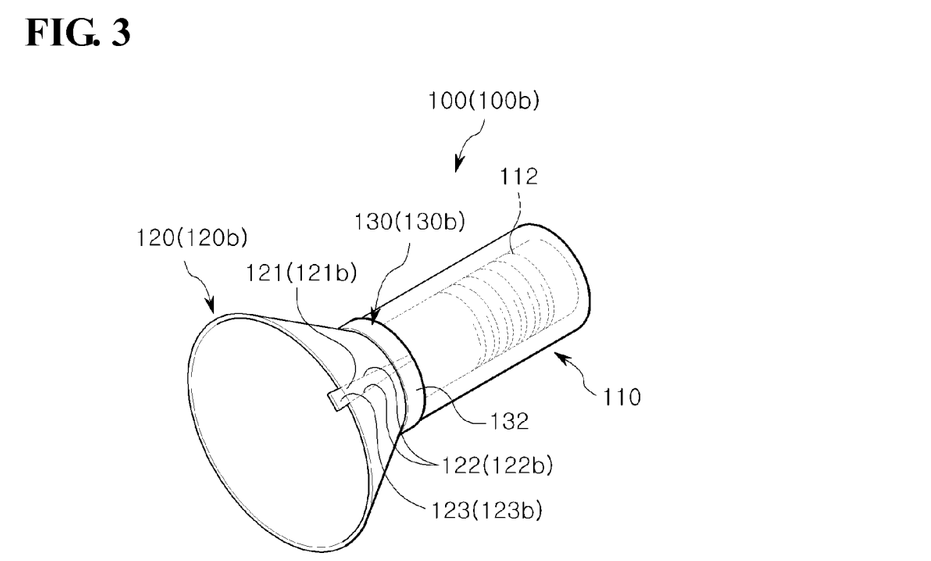
FIG. 3 is a perspective view illustrating another embodiment of the guide unit and the coupling-separating unit illustrated in FIG. 2.
Figure 4:
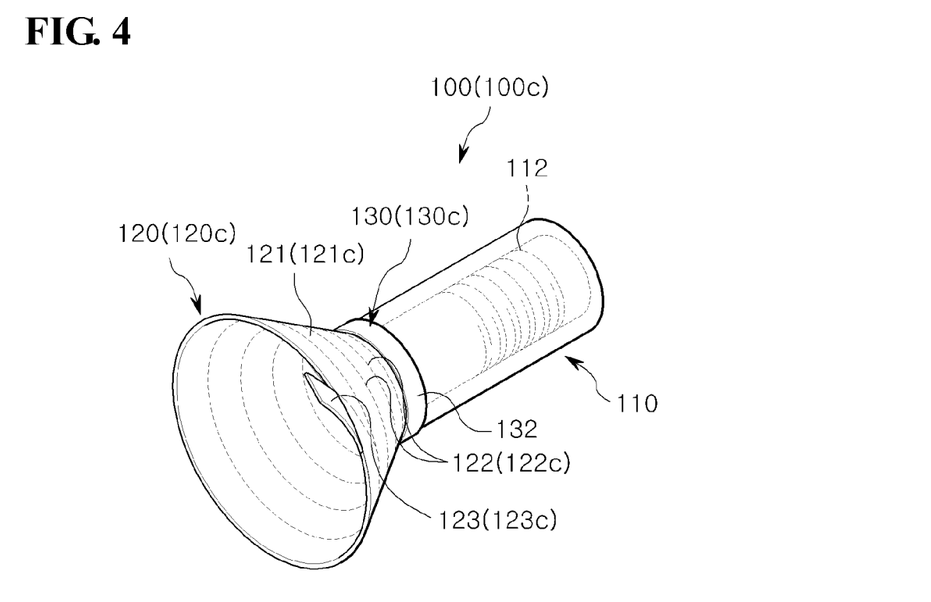
FIG. 4 is a perspective view illustrating another embodiment of the guide unit and the coupling-separating unit illustrated in FIG. 2.

FIG. 2 is an exploded perspective view illustrating an embodiment of the present invention in which the cap unit and the guide unit of the exterior cap illustrated in FIG. 1 are implemented in a separable type, FIG. 3 is a perspective view illustrating another embodiment of the guide unit and the coupling-separating unit illustrated in FIG. 2, and FIG. 4 is a perspective view illustrating another embodiment of the guide unit and the coupling-separating unit illustrated in FIG. 2.

As illustrated in the figures, in the exterior cap 100 (100a, 100b, 100c) for a peritoneal dialysis transfer set according to an embodiment of the present invention, the cap unit 110 and the guide unit 120 (120a, 120b, 120c) are combined by the coupling-separating unit 130 (130a, 130b, 130c). That is, the coupling-separating unit 130 (130a, 130b, 130c) combines the cap unit 110 and the guide unit 120 (120a, 120b, 120c), which are separated from each other, but it can separate the cap unit 110 and the guide unit 120 (120a, 120b, 120c) from each other in accordance with selection of a user. The guide unit 120 (120a, 120b, 120c) separated from the cap unit 110 may be made of PVC, the same as the cap unit 110, but the material is not limited, and for example, it may be made of other materials such as paper or fiber.

As illustrated in FIG. 2, the coupling-separating unit 130 (130a) may have a bonding band 132 and a first separation member 134. The bonding band 132 fixes the cap unit 110 and the guide unit 120 (120a) by bonding their coupling ends. The first separation member 134 extends outward from an end of the bonding band 132 so that a user (patient) can easily hold the bonding band 132 with fingers. A user can separate the cap unit 110 and the guide unit 120 (120a) by taking off the bonding band 132 by pulling the first separation member 134.

As illustrated in FIGS. 3 and 4, the guide unit 120 (120*b*, 120*c*) may further have a first cut-off portion 121 (121*b*, 121*c*). The first cut-off portion 121 (121*b*, 121*c*) is defined by a pair of creases 122 (122*b*, 122*c*) spaced from each other so that at least a side of the guide unit 120 (120*b*, 120*c*) can be partially cut. Further, a first cut-off member 123 (123*b*, 123*c*) protruding outward may be formed at a side of the first cut-off portion 121 (121*b*, 121*c*). A user can easily separate the guide unit 120 (120*b*, 120*c*) from the cap unit 110 by cutting off the first cut-off portion 121 (121*b*, 121*c*), using the first cut-off member 123 (123*b*, 123*c*).

The first cut-off portion 121 (121*b*) may be formed longitudinally at a side of the guide unit 120 (120*b*), as illustrated in FIG. 3. Alternatively, as illustrated in FIG. 4, the first cut-off portion 121 (121*c*) may be formed circumferentially at a side of the guide unit 120 (120*c*), that is, spirally circumferentially formed to grow longitudinally.

In an embodiment of the present invention described above, the first cut-off portion 121 (121*b*, 121*c*) of the guide unit 120 (120*b*, 120*c*) and the bonding band 132 of the coupling-separating unit 130 (130*b*, 130*c*) may be connected to each other. As described above, since the first cut-off portion 121 (121*b*, 121*c*) is connected with the bonding band 132, there is no need for forming the first separation member 134 (see FIG. 2) on the bonding band 132, so the coupling-separating unit 130 can be easily manufactured. Further, when the first cut-off member 121 (121*b*, 121*c*) is taken off the guide unit 120 (120*b*, 120*c*), the bonding band 132 is separated from the cap unit 110, so the cap unit 110 and the guide unit 120 (120*b*, 120*c*) are more simply separated.

Hereinafter, a exterior cap according to another embodiment of the present invention in which a cap unit 210, a guide unit 220 (220*a*, 220*b*, 220*c*) and a coupling-separating unit 230 (230*a*, 230*b*, 230*c*) are implemented in an integral type will be described.

Hereinafter, another embodiment of the present invention will be described with reference to the accompanying drawings.

Figure 5:
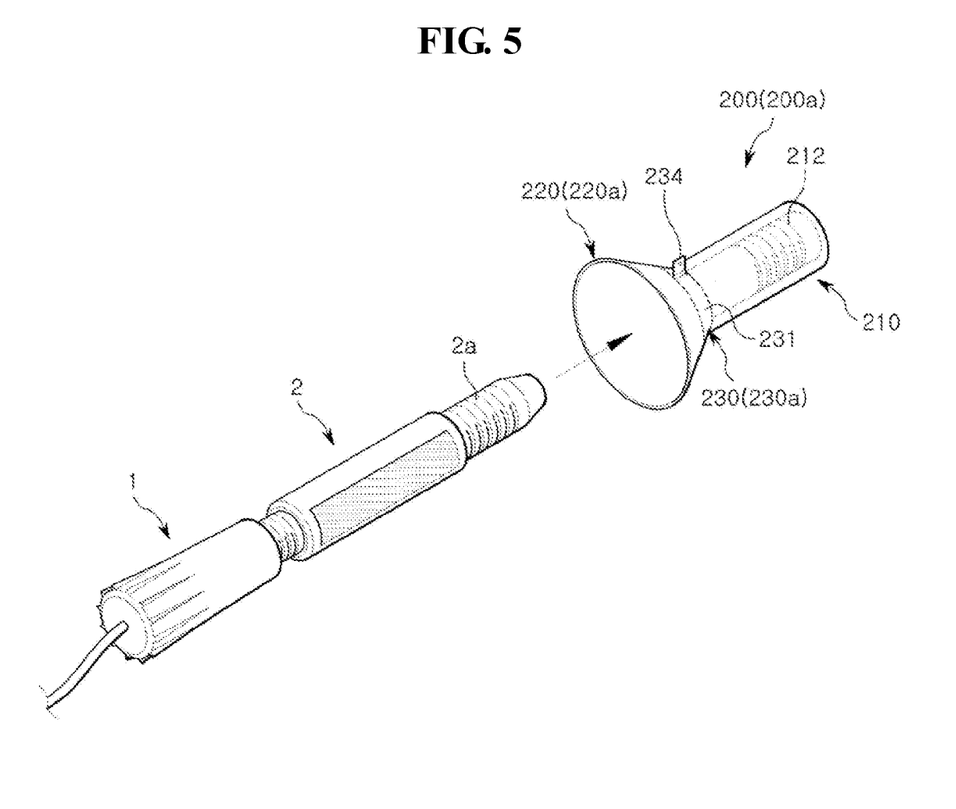
FIG. 5 is an exploded perspective view illustrating an embodiment of the present invention in which the cap unit and the guide unit of the exterior cap illustrated in FIG. 1 are implemented in an integral type.
Figure 6:
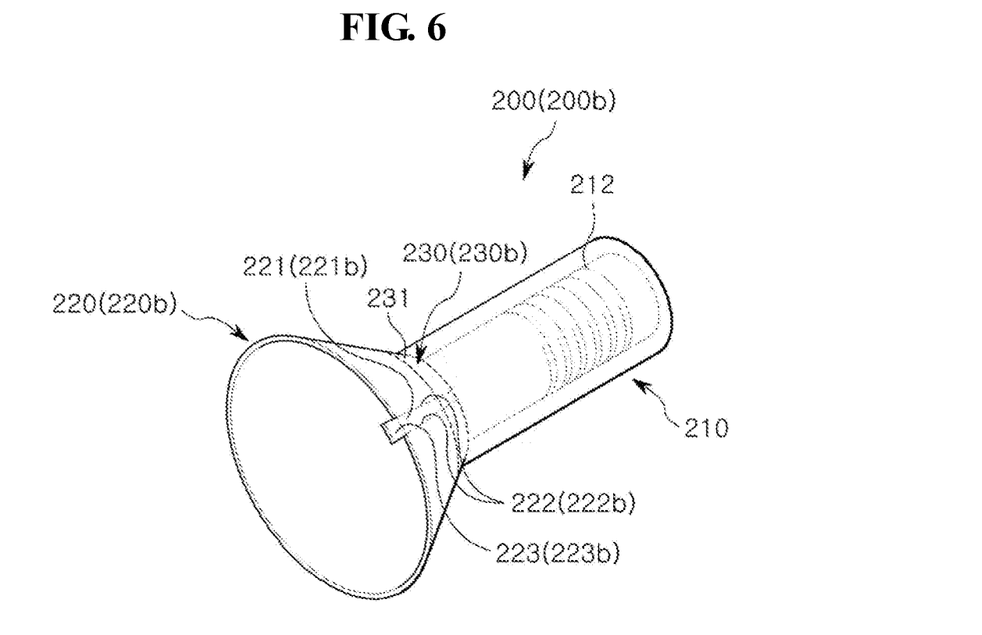
FIG. 6 is a perspective view illustrating another embodiment of the guide unit and the coupling-separating unit illustrated in FIG. 5.
Figure 7:
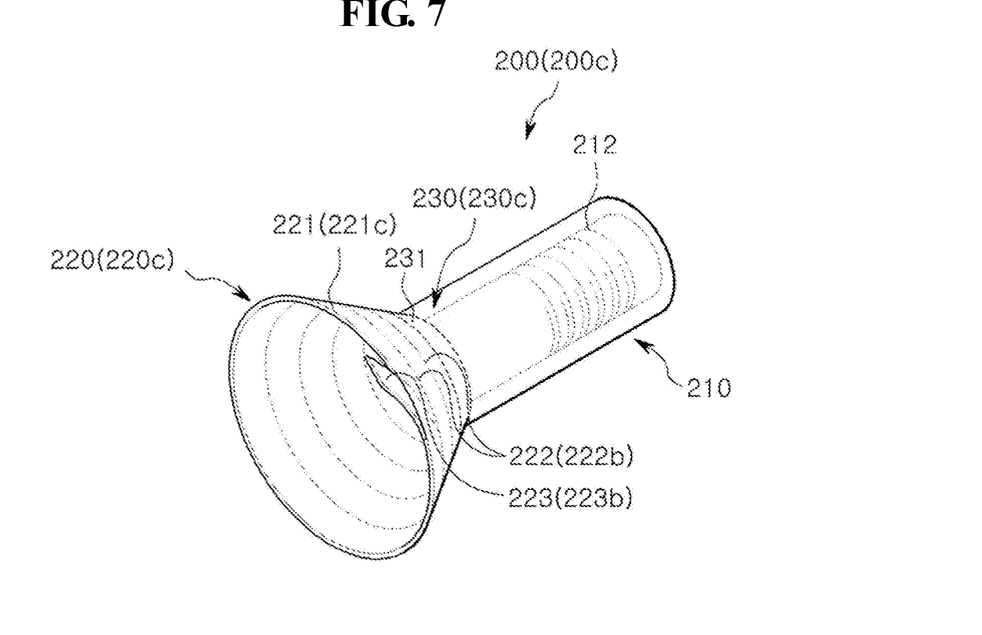
FIG. 7 is a perspective view illustrating another embodiment of the guide unit and the coupling-separating unit illustrated in FIG. 5.

FIG. 5 is an exploded perspective view illustrating an embodiment of the present invention in which the cap unit and the guide unit of the exterior cap illustrated in FIG. 1 are implemented in an integral type, FIG. 6 is a perspective view illustrating another embodiment of the guide unit and the coupling-separating unit illustrated in FIG. 5, and FIG. 7 is a perspective view illustrating another embodiment of the guide unit and the coupling-separating unit illustrated in FIG. 5. The same reference numerals as in FIGS. 1 to 4 indicate the same components having the same operation and effect, so they are not described.

As illustrated in the figures, in the exterior cap 200 (200*a*, 200*b*, 200*c*) for a peritoneal dialysis transfer set according to an embodiment of the present invention, the cap unit 210 and the guide 220 (220*a*, 220*b*, 220*c*) are combined by the coupling-separating unit 230 (230*a*, 230*b*, 230*c*).

As illustrated in FIG. 5, a coupling-separating unit 230 (230*a*) may have a separating portion 231 defined by a pair of creases 233 spaced from each other at the joint of a cap unit 210 and a guide unit 220 (220*a*). Further, the coupling-separating unit 230 (230*a*) may further have a second separation member 234 protruding outward at a side of the separating portion 231. A user (patient) can hold the second separating unit 234 with fingers to separate the separating portion 231.

As illustrated in FIGS. 6 and 7, the guide unit 220 (220*b*, 220*c*) may further have a second cut-off portion 221 (221*b*, 221*c*). The second cut-off portion 221 (221*b*, 221*c*) is defined by a pair of creases 222 (222*b*, 222*c*) spaced from each other so that at least a side of the guide unit 220 (220*b*, 220*c*) can be partially cut. Further, a second cut-off member 223 (223*b*, 223*c*) protruding outward at a side of the second cut-off portion 221 (221*b*, 221*c*) so that a user can hold it is formed at a side of the second cut-off portion 221 (221*b*, 221*c*). A user can easily separate the guide unit 220 (220*b*, 220*c*) from the cap unit 210 by cutting off the second cut-off portion 221 (221*b*, 221*c*), using the second cut-off member 223 (223*b*, 223*c*).

The second cut-off portion 221 (221*b*) may be formed longitudinally at a side of the guide unit 220 (220*b*), as illustrated in FIG. 6. Alternatively, as illustrated in FIG. 7, the second cut-off portion 221 (221*c*) may be formed circumferentially at a side of the guide unit 220 (220*c*), that is, spirally circumferentially formed to grow longitudinally.

Another embodiment of the present invention described above, the second cut-off portion 221 (221*b*, 221*c*) and the separating portion 231 may be connected to each other. Since the second cut-off portion 221 (221*b*, 221*c*) and the separating portion 231 are connected to each other, when the second cut-off portion 221 (221*b*, 221*c*) is taken off the guide unit 220 (220*b*, 220*c*), the separating portion 231 is also taken off the joint between the cap unit 210 and the guide unit 220 (220*b*, 220*c*), such that the cap unit 210 and the guide unit 220 (220*b*, 220*c*) are simply separated.

As described above, according to the exterior caps 100 and 200 for a peritoneal dialysis transfer set of the present invention, a peritoneal dialysis patient can easily couple the exterior caps 100 and 200 to the end connector 2 of the peritoneal transfer set 1, using the guide units 120 and 220 providing an internal space expanding to the end connector 2 of the peritoneal transfer set 1 and can separate the guide units 120 and 220, which are unnecessary after the exterior caps 100 and 200 are coupled, using the coupling-separating units 130 and 230. Therefore, convenience for a user can be increased.

In particular, even a peritoneal dialysis patient accompanied by altered vision due to diabetic retinopathy can easily couple the exterior caps 100 and 200 of the present invention to the end connector 2 of the peritoneal transfer set 1.

Although the present invention has been described with reference to the exemplary embodiments illustrated in the drawings, those are only examples and may be changed and modified into other equivalent exemplary embodiments from the present invention by those skilled in the art. Therefore, the technical protective scope of the present invention should be determined by the scope described in claims.

The present invention can be used for a peritoneal dialysis transfer set.

What is claimed is:

1. A exterior cap of transfer set for peritoneal dialysis which prevents exogenous infection of a peritoneal dialysis patient through a peritoneal transfer set by being hermetically coupled to an end connector of a peritoneal transfer set connected with an interperitonal catheter of the patient, the exterior cap comprising:

a cylindrical cap unit to which the end connector of the peritoneal transfer set is coupled;

a guide unit that is coupled to the cap unit, extends to the peritoneal transfer set to provide an expanding internal space, and guides the end connector of the peritoneal transfer set into the cap unit; and a coupling-separating unit that combines the cap unit and the guide unit with each other and separates the cap unit and the guide unit in accordance with selection of a user, wherein the coupling-separating unit couples the cap unit and the guide unit that are separated, wherein the coupling-separating unit has a bonding band that fixes the cap unit and the guide unit by bonding coupling ends of the cap unit and the guide unit, and a first separation member that extends outward from an end of the bonding band so that a user easily holds the bonding band with fingers.

2. The exterior cap of claim 1, wherein the internal space of the guide unit gradually expands toward the peritoneal transfer set.

3. The exterior cap of claim 2, wherein the guide unit has a conical shape.

4. The exterior cap of claim 1, wherein the guide unit further has a first cut-off portion defined by a pair of creases spaced from each other so that at least a side of the guide unit is partially cut.

5. The exterior cap of claim 4, wherein the guide unit further has a first cut-off member protruding outward at a side of the first cut-off portion so that a user holds the first cut-off member with fingers.

6. The exterior cap of claim 4, wherein the first cut-off portion and the bonding band are connected to each other.

7. The exterior cap of claim 4, wherein the first cut-off portion is formed longitudinally at a side of the guide unit.

8. The exterior cap of claim 4, wherein the first cut-off portion is formed circumferentially at a side of the guide unit.

9. The exterior cap of claim 4, wherein the first cut-off portion is formed spirally circumferentially at a side of the guide unit to grow longitudinally.

10. The exterior cap of claim 4, wherein the guide unit is made of any one selected from a group of paper, PVC, and fiber.

11. The exterior cap of claim 1, wherein the cap unit, the guide unit, and the coupling-separating unit are integrally formed.

12. The exterior cap of claim 11, wherein the coupling-separating unit has:

a separating portion that is defined by a pair of creases spaced from each other at the joint of a cap unit and a guide unit; and a second separation member that protrudes outward at a side of the separating portion so that a user easily holds the separation member with fingers.

13. The exterior cap of claim 11, wherein the guide unit further has a second cut-off portion defined by a pair of creases spaced from each other so that at least a side of the guide unit is partially cut.

14. The exterior cap of claim 13, wherein the guide unit further has a second cut-off member protruding outward at a side of the second cut-off portion so that a user holds the second cut-off member with fingers.

15. The exterior cap of claim 13, wherein the second cut-off portion and the separating portion are connected to each other.

16. The exterior cap of claim 13, wherein the second cut-off portion is formed longitudinally at a side of the guide unit.

17. The exterior cap of claim 13, wherein the second cut-off portion is formed circumferentially at a side of the guide unit.

18. The exterior cap of claim 13, wherein the second cut-off portion is formed spirally circumferentially at a side of the guide unit to grow longitudinally.

* * * * *